United States Patent
Chung et al.

(10) Patent No.: US 11,615,604 B2
(45) Date of Patent: Mar. 28, 2023

(54) METHOD AND APPARATUS FOR MEASURING ENDOLYMPHATIC HYDROPS RATIO OF INNER EAR ORGAN USING ARTIFICIAL NEURAL NETWORK

(71) Applicant: Samsung Life Public Welfare Foundation, Seoul (KR)

(72) Inventors: Won-Ho Chung, Seoul (KR); Baek Hwan Cho, Seoul (KR); Young Sang Cho, Seoul (KR); Chae Jung Park, Seoul (KR)

(73) Assignee: Samsung Life Public Welfare Foundation, Seoul (KR)

(*) Notice: Subject to any disclaimer, the term of this patent is extended or adjusted under 35 U.S.C. 154(b) by 251 days.

(21) Appl. No.: 17/211,371

(22) Filed: Mar. 24, 2021

(65) Prior Publication Data
US 2021/0303900 A1 Sep. 30, 2021

(30) Foreign Application Priority Data
Mar. 26, 2020 (KR) .................. 10-2020-0037062

(51) Int. Cl.
*G06V 10/25* (2022.01)
*G06V 10/26* (2022.01)
(Continued)

(52) U.S. Cl.
CPC .............. *G06V 10/25* (2022.01); *A61B 1/227* (2013.01); *A61B 5/4005* (2013.01);
(Continued)

(58) Field of Classification Search
CPC .. G06V 10/267; G06V 2201/03; A61B 1/227; A61B 5/4005; A61B 5/7271; A61B 2576/00; G06T 7/0014; G16H 50/20
See application file for complete search history.

(56) References Cited

U.S. PATENT DOCUMENTS 10,430,946 B1 10/2019 Zhou et al.
2019/0216308 A1* 7/2019 Senaras ............ A61B 1/000094

FOREIGN PATENT DOCUMENTS

JP 2019-72410 A 5/2019
WO WO 2015/067300 A1 5/2015

OTHER PUBLICATIONS

Liu et al, "ELHnet: a convolutional neural network for classifying cochlear endolymphatic hydrops imaged with optical coherence tomography" (published in Biomedical Optics Express, vol. 8, Issue 10, pp. 4579-4594, Oct. 2017) (Year: 2017).*

* cited by examiner

*Primary Examiner* — Casey L Kretzer
(74) *Attorney, Agent, or Firm* — McCarter & English, LLP

(57) ABSTRACT

Provided are a method and an apparatus for measuring an endolymphatic hydrops ratio of inner ear organs using an artificial neural network. The method of measuring an endolymphatic hydrops ratio includes obtaining a plurality of frame images obtained by capturing inner ear organs, obtaining a plurality of pieces of mask data corresponding to each of the plurality of frame images by inputting the plurality of frame images into a neural network, clustering the plurality of pieces of mask data according to the inner ear organs and obtaining representative images according to the inner ear organs according to certain conditions, and overlapping a target image synthesized by using the plurality of frame images and the representative images according to the inner ear organs so as to measure an endolymphatic hydrops ratio.

10 Claims, 10 Drawing Sheets

(51) Int. Cl.
*G16H 50/20* (2018.01)
*G06T 7/00* (2017.01)
*A61B 5/00* (2006.01)
*A61B 1/227* (2006.01)

(52) U.S. Cl.
CPC .......... *A61B 5/7271* (2013.01); *G06T 7/0014* (2013.01); *G06V 10/267* (2022.01); *G16H 50/20* (2018.01); *A61B 2576/00* (2013.01); *G06V 2201/03* (2022.01)

METHOD AND APPARATUS FOR MEASURING ENDOLYMPHATIC HYDROPS RATIO OF INNER EAR ORGAN USING ARTIFICIAL NEURAL NETWORK

CROSS-REFERENCE TO RELATED APPLICATION

This application claims the benefit of priority under 35 U.S.C. § 119 of Korean Patent Application No. 10-2020-0037062, filed on Mar. 26, 2020, in the Korean Intellectual Property Office, the disclosure of which is incorporated by reference herein in its entirety.

BACKGROUND

1. Field

One or more embodiments relate to a method and an apparatus for measuring an endolymphatic hydrops ratio, and more particularly, to a method and an apparatus for measuring an endolymphatic hydrops ratio by inputting a plurality of frame images obtained by capturing an inner ear organ into an artificial neural network.

2. Description of the Related Art

Meniere's disease is a disease in which symptoms such as dizziness, hearing loss, ringing in the ears, and deafness occur suddenly and repeatedly. Recently, according to the hypothesis that endolymphatic hydrops in the cochlea and vestibular organ that are inner ear organs is the cause of Meniere's disease, experts are diagnosing Meniere's disease when the endolymphatic hydrops ratio is high. However, because, according to the related art, experts have directly detected the cochlea and vestibular organs so as to calculate the endolymphatic hydrops ratio, a considerable amount of time and manpower is wasted.

In particular, the cochlea and vestibular organs occupy a very small area in brain MR images. Therefore, it takes a long time to detect a region of interest (ROI), and the process is complex, and there is a limitation in that objectivity is low because there are differences in opinions for each reader who detects endolymphatic hydrops.

The above background art that is technical information held for derivation of the present disclosure or acquired during the derivation process of the present disclosure is not necessarily known technology disclosed to the general public prior to the filing of the present disclosure.

SUMMARY

One or more embodiments include a method and an apparatus for measuring an endolymphatic hydrops ratio by using only images obtained by capturing the brain without a manual work for extracting an ROI of inner ear organs.

Additional aspects will be set forth in part in the description which follows and, in part, will be apparent from the description, or may be learned by practice of the presented embodiments of the disclosure.

According to one or more embodiments, a method of measuring an endolymphatic hydrops ratio includes obtaining a plurality of frame images obtained by capturing inner ear organs, obtaining a plurality of pieces of mask data corresponding to each of the plurality of frame images by inputting the plurality of frame images into a neural network, clustering the plurality of pieces of mask data according to the inner ear organs and obtaining representative images according to the inner ear organs according to certain conditions, and overlapping a target image synthesized by using the plurality of frame images and the representative images according to the inner ear organs so as to measure an endolymphatic hydrops ratio.

The obtaining of the representative images according to the inner ear organs may further include generating three-dimensional (3D) segmentation corresponding to each of the inner ear organs by using the plurality of pieces of mask data clustered according to the inner ear organs, and the measuring of the endolymphatic hydrops ratio may further include overlapping the target image and the 3D segmentation so as to measure an endolymphatic hydrops ratio.

The obtaining of the representative images according to the inner ear organs may include obtaining mask data having a largest inner ear organ region included in each of the mask data among the plurality of pieces of mask data clustered according to the inner ear organs as representative images of the inner ear organs.

The measuring of the endolymphatic hydrops ratio may include overlapping the target image and the representative image according to the inner ear organs so as to obtain an endolymphatic hydrops detection image; and measuring an endolymphatic hydrops ratio by using pixel data having negative values among inner ear organ mask regions included in the endolymphatic hydrops detection image.

The plurality of frame images may include frame images included in a MR cisternography (MRC) image obtained by capturing the inner ear organs, and the target image may include a HYDROPS image Multiplied with heavily T2-weighted MR cisternography (Hydrops-Mi2) image generated by synthesizing the MRC image and the Hydrops image.

According to one or more embodiments, an apparatus for measuring an endolymphatic hydrops ratio includes a processor, wherein the processor obtains a plurality of frame images obtained by capturing inner ear organs, obtains a plurality of pieces of mask data corresponding to each of the plurality of frame images by inputting the plurality of frame images into a neural network, clusters the plurality of pieces of mask data according to the inner ear organs, obtains representative images according to the inner ear organs according to certain conditions, and overlaps a target image synthesized by using the plurality of frame images and the representative images according to the inner ear organs so as to measure an endolymphatic hydrops ratio.

The processor may further generate three-dimensional (3D) segmentation corresponding to each of the inner ear organs by using the plurality of pieces of mask data clustered according to the inner ear organs and may overlap the target image and the 3D segmentation so as to measure an endolymphatic hydrops ratio.

The processor may obtain mask data having a largest inner ear organ region included in each of the mask data among the plurality of pieces of mask data clustered according to the inner ear organs as representative images of the inner ear organs.

The processor may overlap the target image and the representative image according to the inner ear organs so as to obtain an endolymphatic hydrops detection image and measure an endolymphatic hydrops ration by using pixel data having negative values included in the endolymphatic hydrops detection image.

The plurality of frame images may include frame images included in a MR cisternography (MRC) image obtained by capturing the inner ear organs, and the target image may include a HYDROPS image Multiplied with heavily T2-weighted MR cisternography (Hydrops-Mi2) image generated by synthesizing the MRC image and the Hydrops image.

Other aspects, features, and advantages than those described above will become apparent from the following drawings, the claims, and the detailed description of the invention.

BRIEF DESCRIPTION OF THE DRAWINGS

The above and other aspects, features, and advantages of certain embodiments of the disclosure will be more apparent from the following description taken in conjunction with the accompanying drawings, in which.

DETAILED DESCRIPTION

Figure 1:
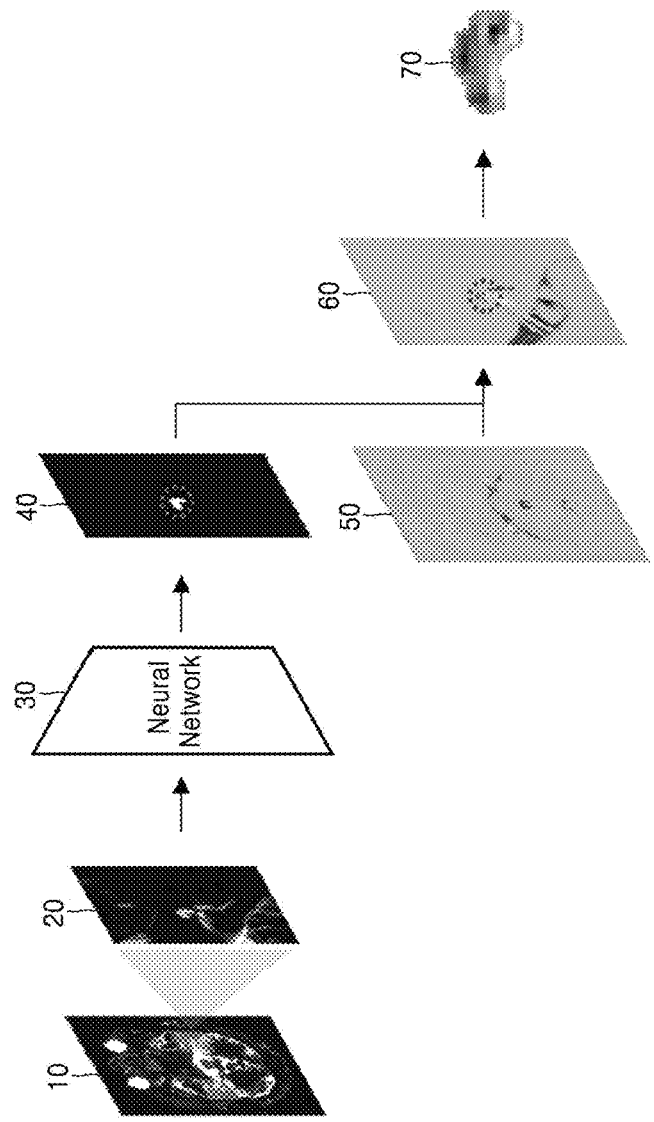
FIG. 1 is a view illustrating a system for measuring an endolymphatic hydrops ratio that performs a method of measuring an endolymphatic hydrops ratio according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

For detailed description of the present disclosure to be described below, the accompanying drawings, which illustrate specific embodiments in which the present disclosure may be practiced, will be referred to. These embodiments will be described in detail so that those skilled in the art are enough to practice the present disclosure. It should be understood that various embodiments of the present disclosure are different from each other, but need not be mutually exclusive. For example, specific shapes, structures, and characteristics described herein can be implemented by being changed to another embodiment from one embodiment without departing from the spirit and scope of the present disclosure. In addition, it should be understood that the positions or arrangements of individual elements in each embodiment may also be changed without departing from the spirit and scope of the present disclosure. Thus, the detailed description to be described below is not made in a limiting sense, and the scope of the present disclosure should be taken as encompassing the scope claimed by the claims and all ranges equivalent thereto. Like reference numerals in the drawings represent the same or similar elements in various aspects.

An artificial intelligence (AI) disclosed in the present disclosure may refer to the field of researching artificial intelligence or the methodology that can create it, and machine learning that is a field of artificial intelligence technology, may be an algorithm as a technical method that allows a computing device to learn through data and to understand a specific object or condition or to find and classify a pattern of data. Machine learning disclosed in the present disclosure can be understood as a meaning including an operation method for learning an artificial intelligence model.

Hereinafter, in order to enable those of ordinary skill in the art to easily implement the present disclosure, various embodiments of the present disclosure will be described in detail with reference to the accompanying drawings.

Hereinafter, a system for measuring an endolymphatic hydrops ratio that performs a method of measuring an endolymphatic hydrops ratio according to an embodiment will be described in detail with reference to FIG. 1.

According to the related art, in order to measure an endolymphatic hydrops ratio to diagnose Meniere's disease, there is a limitation in poor objectivity and accuracy because inner ear organs occupying a very small area in a brain image have been manually detected and the expert directly has measured the endolymphatic hydrops ratio. Thus, hereinafter, a method and an apparatus for measuring an endolymphatic hydrops ratio by using only the brain image without the expert's manual work according to some embodiments will be described.

A frame image 10 obtained by capturing the brain image may be used to measure the endolymphatic hydrops ratio according to an embodiment. In particular, in the method of measuring the endolymphatic hydrops ratio according to some embodiments, a frame image 20 may be extracted from an ear region, and mask data 40 corresponding to a certain inner ear organ region may be obtained by inputting the frame image 20 into a neural network 30. In addition, in the method of measuring the endolymphatic hydrops ratio according to an embodiment, because mask data about a plurality of inner ear organs may be simultaneously extracted, a plurality of pieces of mask data 40 output from the neural network 30 may be clustered for each inner ear organ. For example, mask data corresponding to the vestibular organ and mask data corresponding to the cochlea may be separately clustered, and even mask data about the same inner ear organ may be clustered according to whether it is right or left.

The method of measuring the endolymphatic hydrops ratio according to some embodiments may further include obtaining a clearer image and/or an image about the inner ear organs so as to measure the endolymphatic hydrops ratio. For example, a brain image used as input data of the neural network 30 and an image 50 having a different format from that of the brain image may be synthesized together, so that a target image 60 in which the inner ear organs are more clearly distinguished, may be obtained. Thereafter, the mask data about the already-obtained inner ear organs and the above-described target image may be overlapped so that the endolymphatic hydrops ratio may be measured through analysis of pixel data 70 included in each frame.

Hereinafter, an apparatus for measuring an endolymphatic hydrops ratio will be described in detail with reference to FIG. 2.

In an embodiment, an apparatus 100 for measuring an endolymphatic hydrops ratio may include a memory 101, a processor 102, an input/output interface 103, and a communication module 104. The memory 101 that is a computer readable recording medium may include a permanent mass storage device, such as random access memory (RAM), read only memory (ROM), and a disc drive. In addition, program codes and settings for controlling the apparatus 100 for measuring an endolymphatic hydrops ratio, a plurality of frame images, a plurality of pieces of mask data, and a representative image for each inner ear organ may be temporarily or permanently stored in the memory 101.

The processor 102 may perform basic arithmetic, logic and input/output operations, thereby being configured to process instructions of a computer program. The instructions may be provided to the processor 102 by the memory 101 or the communication module 104. For example, the processor 102 may be configured to execute instructions received according to a program code stored in a storage device such as the memory 101. The processor 102 and components of the processor 102 may control the apparatus 100 for measuring an endolymphatic hydrops ratio so as to perform operations (S110 through S160) of the method of measuring an endolymphatic hydrops ratio of FIG. 3. For example, the processor 102 and the components of the processor 102 may be implemented to execute a code of an operating system of the memory 101 and instructions according to a code of at least one program. Here, the components of the processor 101 may be expressions of different functions of the processor 102 to be performed by the processor 101 according to instructions provided by a program code stored in the apparatus 100 for measuring an endolymphatic hydrops ratio. In an embodiment, the processor 102 of the apparatus 100 for measuring an endolymphatic hydrops ratio may obtain a plurality of frame images by capturing inner ear organs, obtain a plurality of pieces of mask data corresponding to each of the plurality of frame images by inputting the plurality of frame images to a neural network, cluster the plurality of pieces of mask data for each inner ear organ, obtain a representative image for each inner ear organ according to certain conditions, and overlap a target image synthesized using the plurality of frame images and the representative image for each inner ear organ, thereby measuring the endolymphatic hydrops ratio.

The communication module 104 may provide a function for communicating with an external server via a network. In an example, a request generated by the processor 102 of the apparatus 100 for measuring an endolymphatic hydrops ratio according to a program code stored in a recording device such as the memory 101 may be sent to the external server under the control of the communication module 104 via the network. Conversely, control signals, commands, contents, files, etc. provided under the control of a processor of an external server may be received by the apparatus 100 for measuring an endolymphatic hydrops ratio through the communication module 104 via the network. For example, the control signals or commands of the external server received through the communication module 104 may be sent to the processor 102 or the memory 101, and the contents or files may be stored in a storage medium that the apparatus 100 for measuring an endolymphatic hydrops ratio may further include.

In addition, the communication module 104 may communicate with the external server via the network. A communication method is not limited, and the network may be a local area wireless communication network. For example, the network may be a Bluetooth, Bluetooth low energy (BLE), or a Wifi communication network.

In addition, the input/output interface 103 may receiver a user's input and may display output data. The input/output interface 103 according to an embodiment may display mask data and endolymphatic hydrops ratio data of the inner ear organs to a display.

Figure 2:
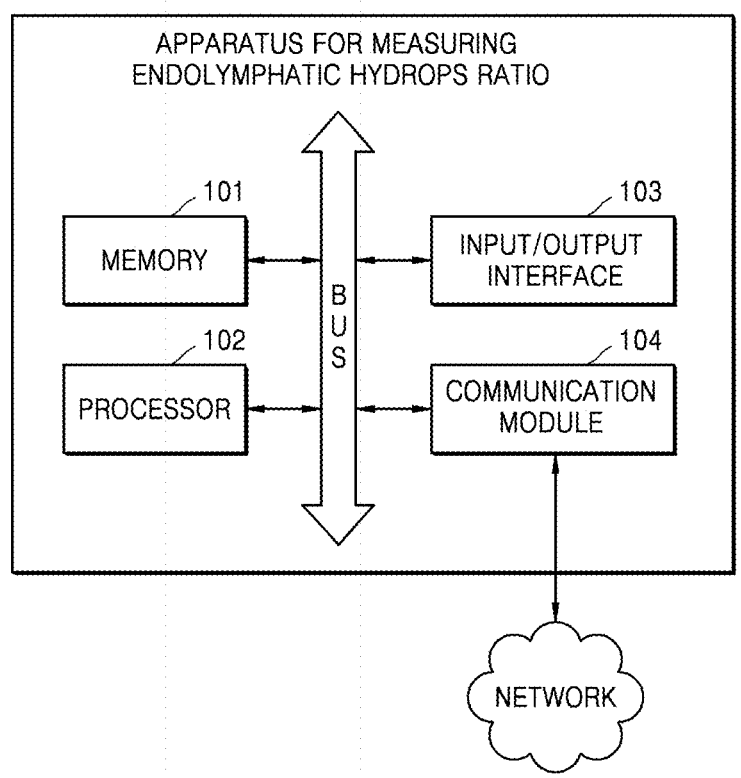
FIG. 2 is a block diagram for describing the configuration and operation of an apparatus for measuring an endolymphatic hydrops ratio according to an embodiment.

In addition, in other embodiments, the apparatus 100 for measuring an endolymphatic hydrops ratio may include more components than the components of FIG. 2. However, there is no need to clearly show most of prior-art components. For example, the apparatus 100 for measuring an endolymphatic hydrops ratio may include a battery and a charging device for supplying power to internal components of the apparatus 100 for measuring an endolymphatic hydrops ratio and may be implemented to include at least part of the above-described input/output devices or may further include other components such as a transceiver, a global positioning system (GPS) module, a variety of sensors, a database, and the like.

Figure 3:
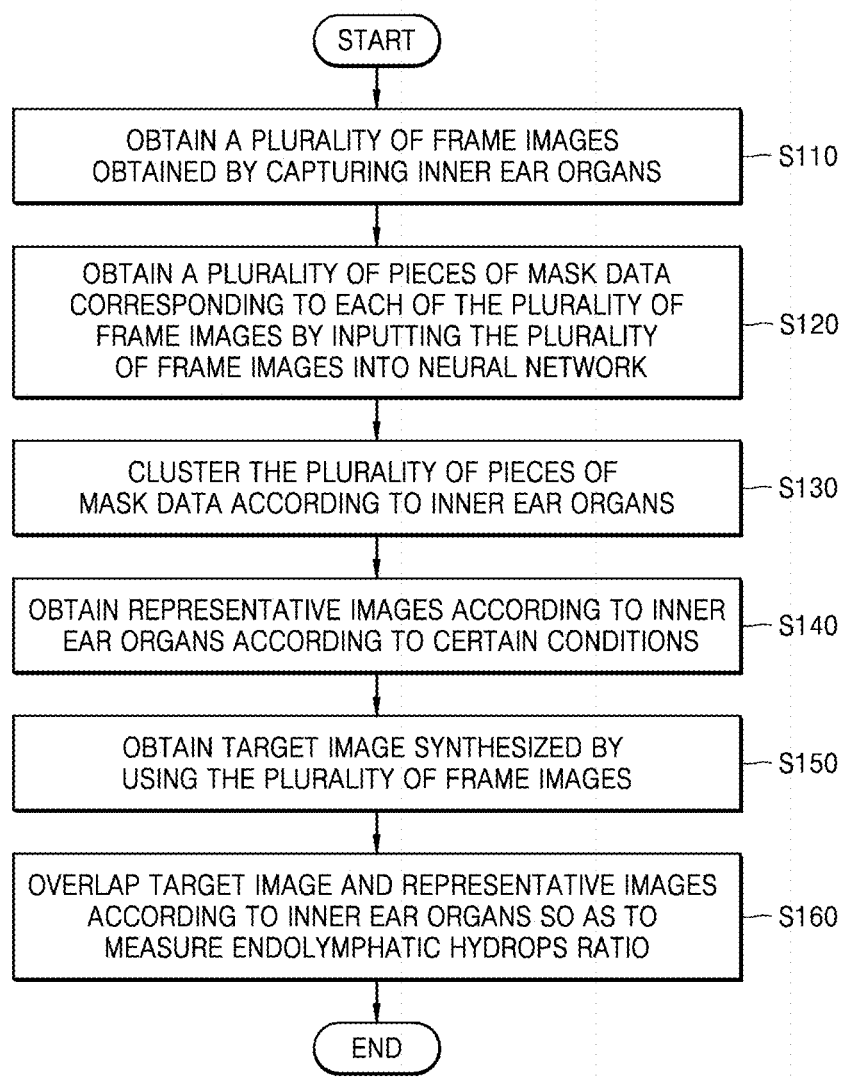
FIG. 3 is a flowchart illustrating a method of measuring an endolymphatic hydrops ratio according to an embodiment.

FIG. 3 is a time series view illustrating a method of measuring an endolymphatic hydrops ratio according to an embodiment.

In operation S110, an apparatus for measuring an endolymphatic hydrops ratio may obtain a plurality of frame images obtained by capturing inner ear organs. The plurality of frame images obtained by capturing inner ear organs may be frame images obtained by capturing an ear region among frame images included in the brain image. In an embodiment, an apparatus for measuring an endolymphatic hydrops ratio may obtain only a frame image corresponding to the ear region among the frame images included in the brain image, and in another embodiment, the apparatus for measuring an endolymphatic hydrops ratio may obtain all of full stack images about the entire brain image and then may extract an image patch about the ear region, and in another embodiment, the apparatus for measuring an endolymphatic hydrops ratio may extract only a frame image including the ear region among a plurality of frame images included in the brain image by using a neural network. In an embodiment, when an image patch corresponding to a specific inner ear organ is extracted from the brain image, a plurality of frame images obtained by capturing the above-described inner ear organ may be frame images included in the image patch. In addition, the brain image may be a brain MR cisternography (MRC) image, for example, and inner ear organs may include the vestibular organ and/or the cochlea. Thus, hereinafter, a method of measuring an endolymphatic hydrops ratio according to some embodiments through the vestibular organ and cochlear images included in the brain MRC image will be described with reference to FIGS. 6 through 10. However, it will be noted that this is just an example for easy understanding of the present disclosure and the format of the brain image or the type and number of inner ear organs are not limited thereto.

In operation S120, the apparatus for measuring an endolymphatic hydrops ratio may obtain a plurality of pieces of mask data each corresponding to a plurality of frame images by inputting a plurality of frame images into the neural network. Each of the plurality of frame images that is a frame image obtained by capturing the inner ear organs included in the ear region may include at least one inner ear organ. Thus, the apparatus for measuring an endolymphatic hydrops ratio according to the present embodiment may obtain mask data in which at least one inner ear organ region included in each frame image is displayed. In this case, the mask data may be output from a neural network based on a convolutional neural network (CNN). For example, the neural network for extracting the mask data of the inner ear organ may include at least one convolution layer, at least one deconvolution layer, and in some embodiments, the neural network may further include a fully connected layer for performing labelling for clustering to be described below. However, it will be noted that this is just an example of the structure of a neural network and according to some embodiments, the structure of the neural network for measuring an endolymphatic hydrops ratio is not limited thereto.

In addition, in an embodiment, the above-described neural network may extract only one target inner ear organ included in each frame image through one calculation, and in another embodiment, all of a plurality of inner ear organ regions included in each frame image may be extracted through one calculation. In this case, the apparatus for measuring an endolymphatic hydrops ratio may generate mask data by using different colors so as to distinguish a plurality of inner ear organs. A method of distinguishing each of the plurality of inner ear organs is not limited, and it is obvious that not only the above-described color but also the thickness and shape of a line may be used.

In operation S130, the apparatus for measuring an endolymphatic hydrops ratio may cluster a plurality of pieces of mask data for each inner ear organ. There is a high possibility that a plurality of inner ear organ regions may be included in each mask data. Thus, the apparatus for measuring an endolymphatic hydrops ratio according to some embodiments may cluster mask data for each inner ear organ. For example, the apparatus for measuring an endolymphatic hydrops ratio may classify mask data corresponding to each of the left vestibular organ, the right vestibular organ, the left cochlea, and the right cochlea.

In operation S140, the apparatus for measuring an endolymphatic hydrops ratio may obtain a representative image for each inner ear organ according to certain conditions. In an embodiment, the apparatus for measuring an endolymphatic hydrops ratio may extract a representative image that most clearly displays a corresponding inner ear organ among the mask data clustered for each inner organ. In an embodiment, the apparatus for measuring an endolymphatic hydrops ratio may select mask data including a largest region of interest (ROI) as a representative image of the corresponding inner ear organ. In an embodiment, each mask data may display an ROI corresponding to an inner ear organ region. Thus, the apparatus for measuring an endolymphatic hydrops ratio according to the present embodiment may select mask data having a largest ROI as a representative image that most clearly displays an inner ear organ.

In operation S150, the apparatus for measuring an endolymphatic hydrops ratio may obtain a target image synthesized using a plurality of frame images. In the present embodiment, the apparatus for measuring an endolymphatic hydrops ratio may further synthesize an image having a different format from that of a plurality of frame images used to more exactly detect the inner ear organ in operation S110, thereby obtaining the target image. For example, when the above-described plurality of images are frame images included in the brain MRC image, the apparatus for measuring an endolymphatic hydrops ratio may synthesize the above-described brain MRC image and a Hydrops image, thereby obtaining the target image. In this case, the obtained target image may be an image having a format of HYDROPS image Multiplied with heavily T2-weighted MR cisternography (Hydorps-Mi2). More specifically, the apparatus for measuring an endolymphatic hydrops image according to the present embodiment may perform a multiplication operation on the MRC image and the Hydrops image in units of pixel, thereby obtaining the target image. The above-described target image may have a higher contrast-to-noise ratio (CNR) than the frame images. However, it will be noted that the format of the above-described image is just an example for easy understanding of the present disclosure and the format of the frame image and the format of the target image according to some embodiments are not limited thereto.

In addition, in some embodiments, operation S150 may be performed independently from operations S110 through S140 described above. Thus, one among operations S110 through S140 and operation S150 may be simultaneously performed, and operation S150 may also be performed prior to operations S110 through S140, and after operations S110 through S140, operation S150 may also be performed.

In operation S160, the apparatus for measuring an endolymphatic hydrops ratio may overlap the target image and the representative image for each inner ear organ, thereby measuring the endolymphatic hydrops ratio. In an embodiment, the apparatus for measuring an endolymphatic hydrops ratio may overlap the generated target image and the representative image obtained in operation S140. Subsequently, the apparatus for measuring an endolymphatic hydrops ratio may measure an endolymphatic hydrops ratio of an inner ear organ included in the target image by using the representative image. The method of measuring an endolymphatic hydrops ratio will be described below in more detail with reference to FIG. 5.

Figure 4:
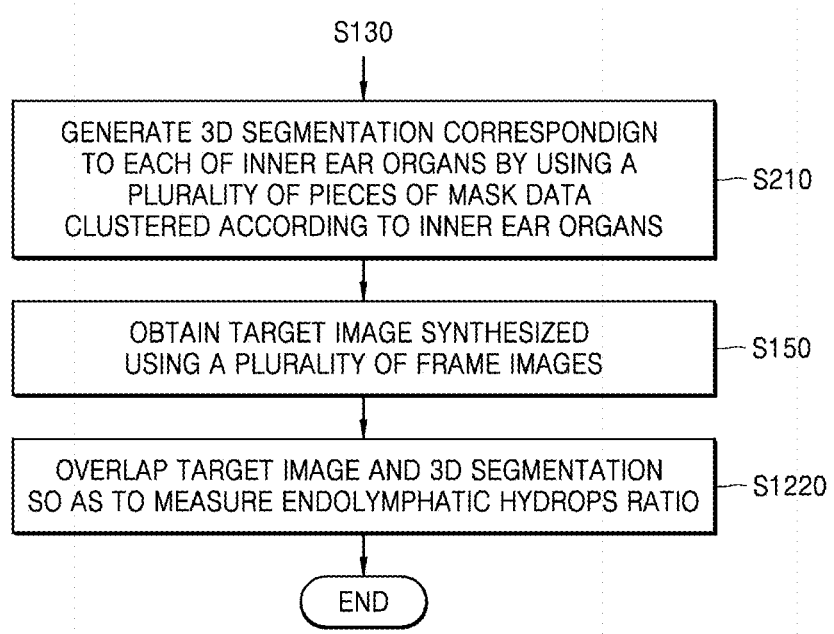
FIGS. 4 and 5 are views for describing some operations of FIG. 3 in detail.

Hereinafter, the method of measuring an endolymphatic hydrops ratio of inner ear organs by using a three-dimensional (3D) segmentation according to an embodiment will be described in detail with reference to FIG. 4.

In operation S210, the apparatus for measuring an endolymphatic hydrops ratio may generate 3D segmentation corresponding to each of inner ear organs by using a plurality of pieces of mask data clustered for each inner ear organ. The apparatus for measuring an endolymphatic hydrops ratio according to the present embodiment may generate 3D segmentation corresponding to the inner ear organs. In this case, the apparatus for measuring an endolymphatic hydrops ratio does not need to obtain a representative image, unlike in operations S110 through S140 shown in FIG. 3. Thus, the apparatus for measuring an endolymphatic hydrops ratio according to the present embodiment may obtain one 3D segmentation corresponding to each of the inner ear organs by using a plurality of pieces of mask data clustered for each inner ear organ. For example, when the plurality of pieces of mask data clustered based on the left vestibular organ, the right vestibular organ, the left cochlea and the right cochlea are obtained, the apparatus for measuring an endolymphatic hydrops ratio may generate 3D segmentation corresponding to each of the left vestibular organ, the right vestibular organ, the left cochlea and the right cochlea.

In addition, in operation S150, the apparatus for measuring an endolymphatic hydrops ratio may obtain a target image by using a plurality of frame images. As described above, the apparatus for measuring an endolymphatic hydrops ratio may perform operation S150 independently from operation S210 described above, thereby obtaining a target image. In this case, operation S210 and operation S150 may be simultaneously performed, and operation S150 may be performed prior to operation S210, and after operation S210 is performed, operation S150 may also be performed.

In operation S220, the apparatus for measuring an endolymphatic hydrops ratio may overlap the target image and the 3D segmentation, thereby measuring the endolymphatic hydrops ratio. In an embodiment, the apparatus for measuring an endolymphatic hydrops ratio may generate 3D data corresponding to each inner ear organ by using a full stack of a plurality of frame images included in the target image and may measure the endolymphatic hydrops ratio by overlapping the above-described 3D data and the 3D segmentation obtained in operation S210. In this case, the apparatus for measuring an endolymphatic hydrops ratio may measure the endolymphatic hydrops ratio of the inner ear organ by using 3D pixels having the shape of a cuboid.

In addition, a neural network according to some embodiments may detect 3D segmentation by using data having a 3D format from a neural network learning stage, and even in this case, the apparatus for measuring an endolymphatic hydrops ratio may detect an inner ear organ included in the 3D segmentation. In the present embodiment, the above-described neural network may be a neural network having a 3D CNN structure.

Figure 5:
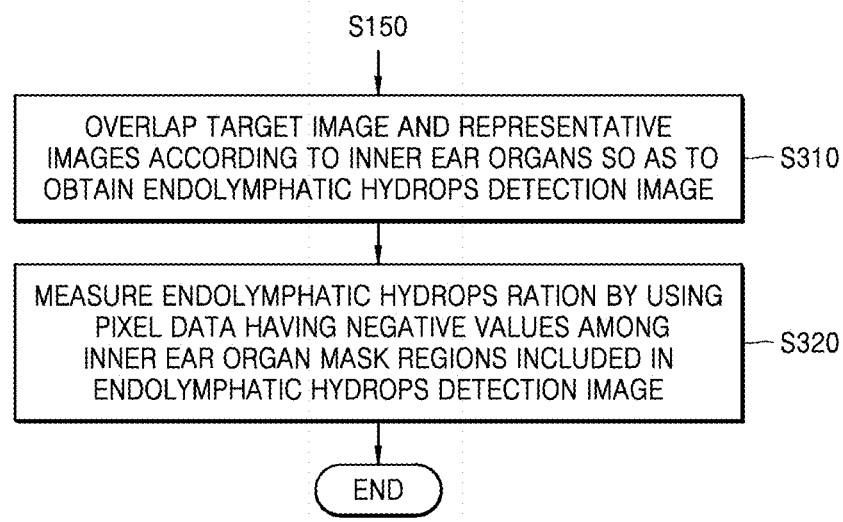

Hereinafter, a method for measuring an endolymphatic hydrops ratio according to an embodiment will be described in detail with reference to FIG. 5.

In operation S310, the apparatus for measuring an endolymphatic hydrops ratio may overlap the target image and the representative image for each inner ear organ, thereby obtaining an endolymphatic hydrops detection image. More specifically, the apparatus for measuring an endolymphatic hydrops ratio may obtain an endolymphatic hydrops detection image including pixel data included in the ROI with respect to a frame image of a target image corresponding to the above-described representative image.

Subsequently, in operation S320, the apparatus for measuring an endolymphatic hydrops ratio may measure the endolymphatic hydrops ratio by using pixel data having negative values included in the endolymphatic hydrops detection image. In the present embodiment, the apparatus for measuring an endolymphatic hydrops ratio may measure the endolymphatic hydrops ratio by using values of pixels included in the ROI included in the above-described endolymphatic hydrops detection image. In an embodiment, the endolymphatic hydrops ratio may be measured by using the ratio of the number of pixels having negative values among the number of image pixels included in the above-described ROI.

Figure 6:
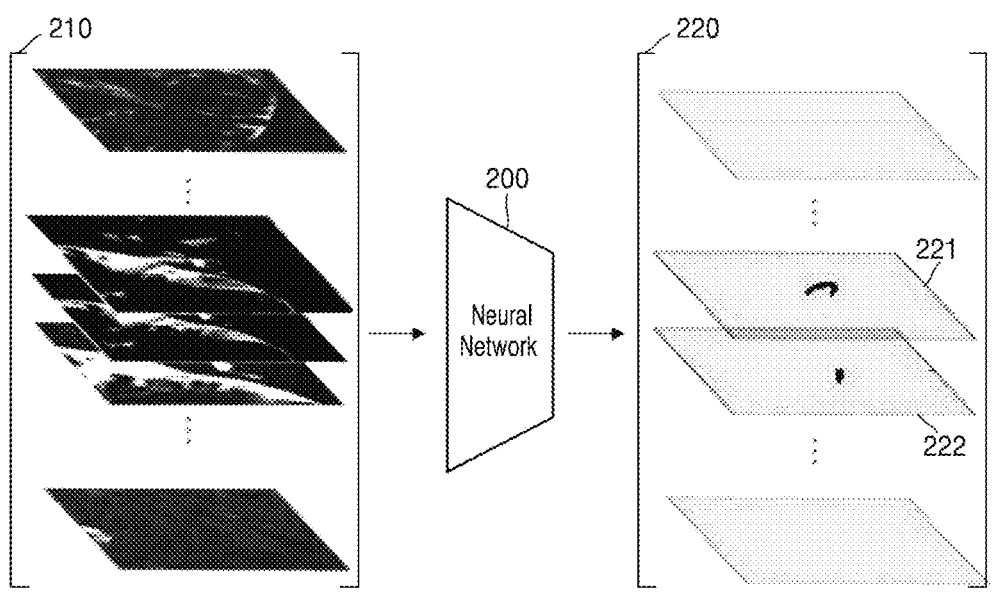
FIG. 6 is a view for describing a method of acquiring a plurality of master data by using a neural network according to an embodiment.

Hereinafter, a method of obtaining a plurality of pieces of mask data by using a neural network according to an embodiment will be described in detail with reference to FIG. 6.

According to an embodiment, after a plurality of frame images 210 are obtained by capturing the inner ear organs, the apparatus for measuring an endolymphatic hydrops ratio may obtain a plurality of pieces of mask data 220 by inputting a plurality of frame images described above into a neural network 200 having a CNN structure. In this case, the plurality of pieces of mask data 220 output from the neural network may correspond to each of the plurality of frame images 210. In addition, each of the plurality of pieces of mask data 220 may include an ROI corresponding to one or more inner ear organ regions. The neural network 200 for detecting the inner ear organ regions may be pre-trained by using a plurality of frames images included in the MRC image and a plurality of pieces of mask data in which the inner ear organ regions are displayed.

The plurality of frame images 210 obtained by capturing the inner ear organs may be frame images obtained by capturing the ear region among the frame images included in the brain image. In an embodiment, the apparatus for measuring an endolymphatic hydrops ratio may obtain only the frame images corresponding to the ear region among the frame images included in the brain image, and in another embodiment, after all of full stack images about the entire brain image are obtained, the apparatus for measuring an endolymphatic hydrops ratio may extract an image patch about the ear region, and in another embodiment, the apparatus for measuring an endolymphatic hydrops ratio may extract only the frame image 210 including the ear region among the plurality of frame images included in the brain image by using the neural network. In an embodiment, when an image patch corresponding to a specific inner ear organ is extracted from the brain image, a plurality of frame images obtained by capturing the above-described inner ear organ may be frame images included in the image patch. For example, the brain image may be a brain MRC image, for example, and the inner ear organ may include the vestibular organ and/or the cochlea, for example. In addition, in an embodiment, the apparatus for measuring an endolymphatic hydrops ratio may obtain mask data 220 in which one or more inner ear organ regions are displayed. In this case, the mask data 220 may be output from the neural network 200 based on a CNN. The above-described neural network 200 may include at least one convolution layer and at least one deconvolution layer. In some embodiments, the neural network 200 may further include a fully connected layer that performs labelling for clustering to be described below.

An example of frame images and mask data according to some embodiments will be described with reference to FIG. 7.

Referring to the drawing, an apparatus for measuring an endolymphatic hydrops ratio according to an embodiment may extract only one target inner ear organ region included in each frame image through one calculation. However, in another embodiment, all of a plurality of inner ear organ regions include in each frame image may also be extracted through one calculation. In this case, the apparatus for measuring an endolymphatic hydrops ratio may generate mask data by using different colors so as to distinguish a plurality of inner ear organs. A method of distinguishing each of the plurality of inner ear organs is not limited, and it is obvious that not only the above-described color but also the thickness and shape of a line may be used.

In addition, an apparatus for measuring an endolymphatic hydrops ratio according to an embodiment may cluster a plurality of pieces of mask data for each inner ear organ. There is a high possibility that a plurality of inner ear organ regions may be included in each mask data. Thus, the apparatus for measuring an endolymphatic hydrops ratio according to an embodiment may cluster mask data for each inner ear organ. For example, the apparatus for measuring an endolymphatic hydrops ratio may classify mask data corresponding to each of the left vestibular organ, the right vestibular organ, the left cochlea, and the right cochlea.

Subsequently, the apparatus for measuring an endolymphatic hydrops ratio may obtain a representative image for each inner ear organ according to certain conditions. In an embodiment, the apparatus for measuring an endolymphatic hydrops ratio may extract a representative image that most clearly displays a corresponding inner ear organ among the mask data clustered for each inner organ. The above-described certain conditions for selecting the representative image may be variously set according to an obtained frame image, an inner ear organ, or a user's purpose. In an embodiment, the apparatus for measuring an endolymphatic hydrops ratio may select mask data including a largest ROI as a representative image of a corresponding inner ear organ. In an embodiment, each mask data may display an ROI corresponding to an inner ear organ region. Thus, the apparatus for measuring an endolymphatic hydrops ratio according to the present embodiment may select mask data having a largest ROI as a representative image that most clearly displays an inner ear organ.

Figure 7:
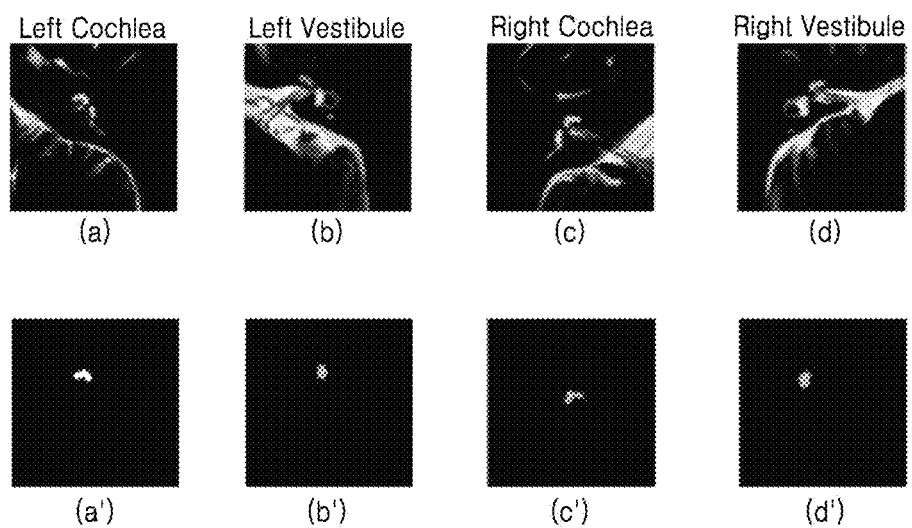
FIG. 7 is a view for describing a method of acquiring a representative image for each inner ear organ according to an embodiment.

For example, as shown in FIG. 7, a representative image a' of the left vestibular organ obtained based on a frame image a of the left vestibular organ may include the largest ROI corresponding to the left vestibular organ, and a representative image b' of the right vestibular organ obtained based on a frame image b of the right vestibular organ may include the largest ROI corresponding to the right vestibular organ, and a representative image c' of the left cochlea obtained based on a frame image c of the left cochlea may include the largest ROI corresponding to the left cochlea, and a representative image d' of the right cochlea obtained based on a frame image d of the right cochlea may include the largest ROI corresponding to the right cochlea.

Figure 8:
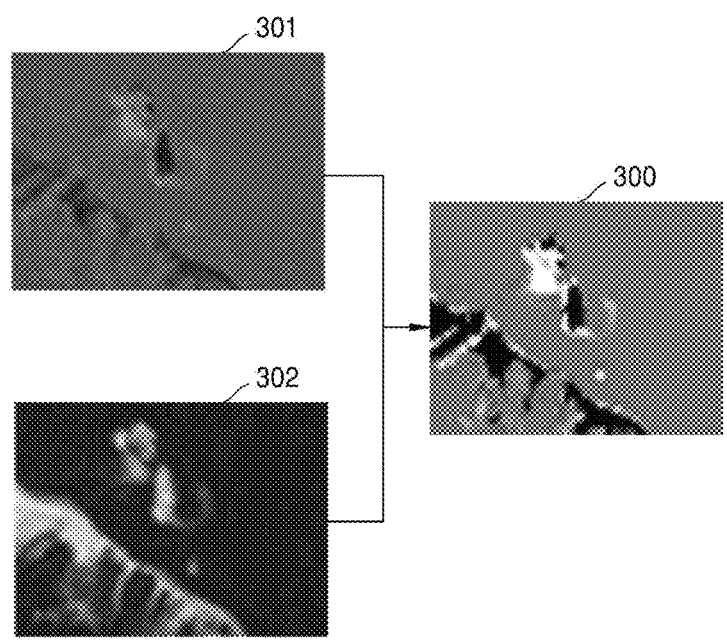
FIG. 8 is a view for describing a method of acquiring a target image by using a plurality of frame images according to an embodiment.

Hereinafter, a method of obtaining a target image according to some embodiments will be described in detail with reference to FIG. 8.

An apparatus for measuring an endolymphatic hydrops ratio may obtain a target image synthesized by using a plurality of frame images in operation S150. In the present embodiment, the apparatus for measuring an endolymphatic hydrops ratio may obtain a target image by further synthesizing an image having a different format from that of a plurality of frame images so as to more exactly detect inner ear organs. For example, when the plurality of frame images described above are frame images included in an MRC image 301, the apparatus for measuring an endolymphatic hydrops ratio may synthesize an image having a different format from that of the above-described MRC image 301 among images obtained by capturing the inner ear organs and a plurality of frame images obtained through the above-described MRC image 301. For example, the apparatus for measuring an endolymphatic hydrops ratio may synthesize the above-described brain MRC image 301 and a Hydrops image 302, thereby obtaining a target image 300. In this case, the obtained target image 300 may be an image having a format of Hydrops-Mi2. More specifically, the apparatus for measuring an endolymphatic hydrops ratio according to the present embodiment may obtain a target image by performing a multiplication operation on the MRC image 301 and the hydrops image 302 in units of a pixel. The above-described target image may have a higher contrast-to-noise ratio (CNR) compared to the image frames. However, it will be noted that the format of the above-described image is just an example for easy understanding of the present disclosure and the format of the frame image and the format of the target image according to some embodiments are not limited thereto.

Figure 9:
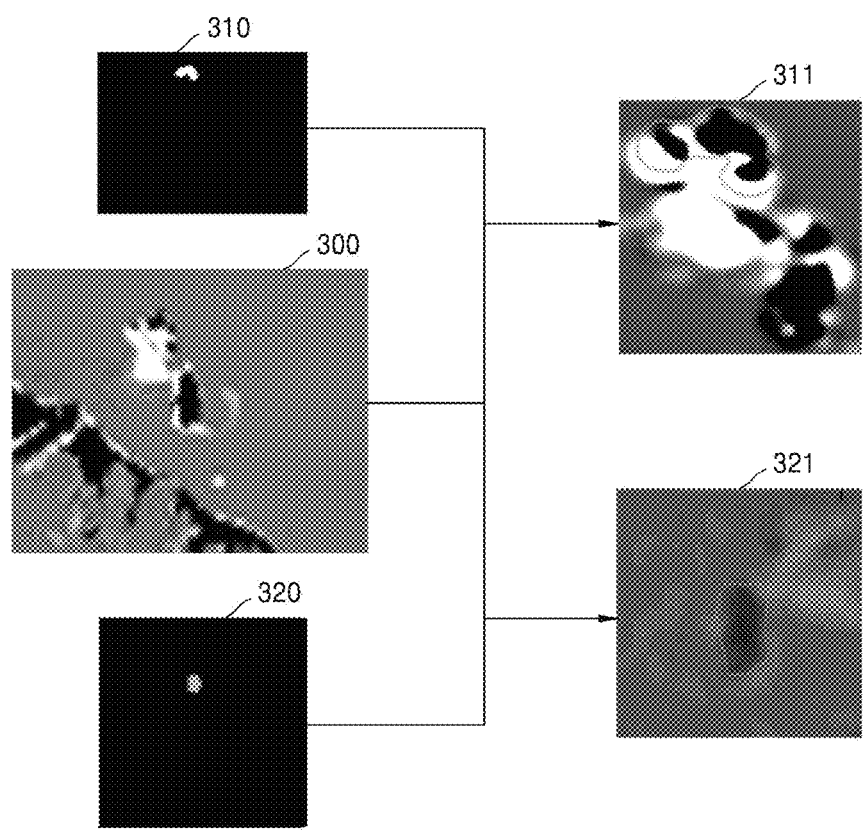
FIG. 9 is a view illustrating a method of measuring an endolymphatic hydrops ratio according to an embodiment.

FIG. 9 is a view illustrating a method of measuring an endolymphatic hydrops ratio according to an embodiment.

An apparatus for measuring an endolymphatic hydrops ratio according to an embodiment may overlap the target image 300 and the representative images 310 and 320 according to an inner ear organ, thereby obtaining endolymphatic hydrops detection images 311 and 321 for each inner ear organ. More specifically, the apparatus for measuring an endolymphatic hydrops ratio may obtain pixel data of an ROI corresponding to an inner ear organ included in the representative images with respect to the frame images of the target image 300 corresponding to the above-described representative images 310 and 320. In an embodiment, the apparatus for measuring an endolymphatic hydrops ratio may sequentially or simultaneously perform an operation of obtaining a first endolymphatic hydrops detection image 311 by using the representative image 310 of a first inner ear organ and the target image 300 and an operation of obtaining a second endolymphatic hydrops detection image 321 by using the representative image 320 of a second inner ear organ and the target image 300.

Subsequently, the apparatus for measuring an endolymphatic hydrops ratio may measure the endolymphatic hydrops ratio by using pixel data having negative values included in the endolymphatic hydrops detection images 311 and 321. In the present embodiment, the apparatus for measuring an endolymphatic hydrops image may measure the endolymphatic hydrops ratio by using values of pixels included in the ROI included in the above-described endolymphatic hydrops detection images 311 and 321. In an embodiment, the endolymphatic hydrops ratio may be measured by using the ratio of the number of pixels having negative values among the number of image pixels included in the above-described ROI.

Figure 10:
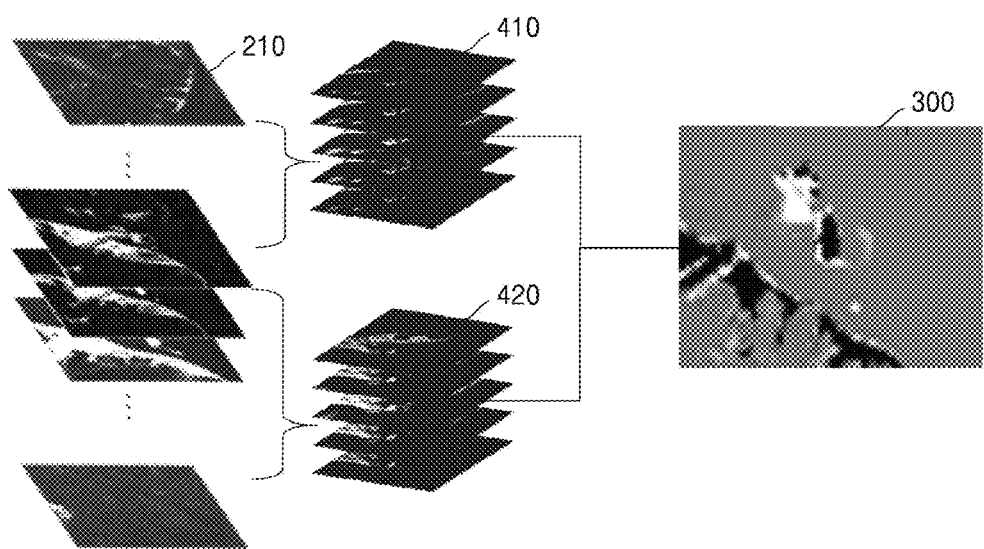
FIG. 10 is a view for describing a method of measuring an endolymphatic hydrops ratio by generating a three-dimensional (3D) segmentation for each inner ear organ according to an embodiment.

Hereinafter, a method of measuring an endolymphatic hydrops ratio of inner ear organs by using 3D segmentation corresponding to inner ear organs according to another embodiment will be described in detail with reference to FIG. 10.

In an embodiment, the apparatus for measuring an endolymphatic hydrops ratio may generate 3D segmentations 410 and 420 corresponding to each of the inner ear organs by using a plurality of frame images 210 clustered for each inner ear organ. The apparatus for measuring an endolymphatic hydrops ratio according to the present embodiment may generate 3D segmentation corresponding to the inner ear organs. In this case, unlike in the above-described embodiment, the apparatus for measuring an endolymphatic hydrops ratio does not need to obtain a representative image for each inner ear organ. Thus, the apparatus for measuring an endolymphatic hydrops ratio according to the present embodiment may overlap a plurality of frame images 210 clustered for each inner ear organ, thereby obtaining 3D segmentations 410 and 420 corresponding to each of the inner ear organs. For example, when the plurality of pieces of mask data clustered based on the left vestibular organ, the right vestibular organ, the left cochlea and the right cochlea are obtained, the apparatus for measuring an endolymphatic hydrops ratio may generate 3D segmentation corresponding to each of the left vestibular organ, the right vestibular organ, the left cochlea and the right cochlea.

In addition, a neural network according to some embodiments may detect 3D segmentation by using data having a 3D format from a neural network learning stage, and even in this case, the apparatus for measuring an endolymphatic hydrops ratio may detect an inner ear organ included in the 3D segmentation. In the present embodiment, the above-described neural network may be a neural network having a 3D CNN structure.

In another embodiment, the apparatus for measuring an endolymphatic hydrops ratio may obtain 3D segmentation by using a plurality of pieces of mask data output from the neural network. In this case, the apparatus for measuring an endolymphatic hydrops ratio may generate 3D segmentation based on an ROI of inner ear organs included in the above-described mask data.

Hereinafter, 3D segmentation to be described below will be described on the assumption that the ROI is detected through 3D CNN or is generated by using a plurality of pieces of mask data including the ROI.

The apparatus for measuring an endolymphatic hydrops ratio may overlap the target image 300 and the 3D segmentations 410 and 420, thereby measuring the endolymphatic hydrops ratio. In an embodiment, the apparatus for measuring an endolymphatic hydrops ratio may generate 3D data corresponding to each inner ear organ by using a full stack of a plurality of frame images included in the target image 300 and may overlap the above-described 3D data and the 3D segmentations 410 and 420, thereby measuring the endolymphatic hydrops ratio. In this case, the apparatus for measuring an endolymphatic hydrops ratio may measure the endolymphatic hydrops ratio of the inner ear organ by using 3D pixels. In this case, the shape of the 3D pixels may be a hexagonal shape. However, this is just an example, and it is obvious that the endolymphatic hydrops ratio may be measured through volume measurement of 3D objects corresponding to the inner ear organs by using the 3D pixels.

The above-described apparatus may be implemented with hardware components, software components, and/or a combination of hardware components and software components. For example, the apparatus and the components described in the embodiments may be implemented by using one or more general-purpose computers or a specific purpose computer, like in a processor, a controller, an arithmetic logic unit (ALU), a digital signal processor, a microcomputer, a field programmable gate array (FPGA), a programmable logic unit (PLU), a microprocessor, or any device for executing and responding instructions. A processing device may perform an operating system (OS) and one or more software applications to be performed on the operating system (OS). In addition, the processing device may access, store, manipulate, process, and generate data in response to the execution of software. For convenience of understanding, although it is sometimes described that only one processing device is used, one of ordinary skill in the art will appreciate that the processing device may include a plurality of processing elements and/or multiple types of processing elements. For example, the processing device may be a plurality of processors, a single processor, or a single controller. Also, other processing configurations, such as a parallel processor, are possible.

The software may include a computer program, code, and instructions, or a combination of one or more thereof, configure the processing device to operate as desired, or instruct the processing device independently or collectively. The software and/or data may be interpreted by the processing device or may be permanently or temporarily embodied to any type of machine, component, physical device, virtual equipment, computer storage medium or device, or single wave to be transmitted, so as to provide instructions or data to the processing device. The software may be distributed on a computer system connected via a network and stored or executed in a distributed manner. The software and data may be stored on one or more computer readable recording mediums.

A method according to an embodiment may be implemented in the shape of program instructions that may be executed by using various computer units and may be recorded on a computer readable medium. The computer readable medium may include program instructions, data files, data structures, and the like alone or in combination. The program instructions recorded on a medium may be specifically designed and configured for the embodiment, or may be known and usable to those skilled in computer software. Examples of computer readable recording mediums may include magnetic media such as hard disks, floppy disks, and magnetic tapes, optical media such as CD-ROMs and DVDs, magneto-optical media such as floptical disks, and hardware devices specially configured to store and execute program instructions such as ROM, RAM, flash memory, and the like. Examples of program instructions include not only machine language codes such as those produced by a compiler, but also high-level language codes that can be executed by a computer using an interpreter or the like. The above-described hardware devices may be configured to operate as one or more software modules to perform the operation of the embodiment, and vice versa.

As described above, although the embodiments have been described by the limited embodiments and drawings, various modifications and variations are possible from the above description to those of ordinary skill in the art. For example, the described techniques are performed in an order different from the described method, and/or components such as a system, structure, device, circuit, etc. described are coupled or combined in a form different from the described method, or even if the components are substituted by other components or an equivalent, an appropriate result can be achieved.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from the spirit and scope of the disclosure as defined by the following claims.

What is claimed is:

1. A method of measuring an endolymphatic hydrops ratio, the method comprising:
    obtaining a plurality of frame images obtained by capturing inner ear organs;
    obtaining a plurality of pieces of mask data corresponding to each of the plurality of frame images by inputting the plurality of frame images into a neural network;
    clustering the plurality of pieces of mask data according to the inner ear organs and obtaining representative images according to the inner ear organs according to certain conditions; and
    overlapping a target image synthesized by using the plurality of frame images and the representative images according to the inner ear organs
    so as to measure
    an endolymphatic hydrops ratio.

2. The method of claim 1, wherein
    the obtaining of the representative images according to the inner ear organs further comprises generating three-dimensional (3D) segmentation corresponding to each of the inner ear organs by using the plurality of pieces of mask data clustered according to the inner ear organs, and the measuring of the endolymphatic hydrops ratio further comprises overlapping the target image and the 3D segmentation so as to measure an endolymphatic hydrops ratio.

3. The method of claim 1, wherein the obtaining of the representative images according to the inner ear organs comprises obtaining mask data having a largest inner ear organ region included in each of the mask data among the plurality of pieces of mask data clustered according to the inner ear organs as representative images of the inner ear organs.

4. The method of claim 1, wherein the measuring of the endolymphatic hydrops ratio comprises overlapping the target image and the representative image according to the inner ear organs so as to obtain an endolymphatic hydrops detection image; and measuring an endolymphatic hydrops ratio by using pixel data having negative values among inner ear organ mask regions included in the endolymphatic hydrops detection image.

5. The method of claim 1, wherein the plurality of frame images comprise frame images included in a MR cisternography (MRC) image obtained by capturing the inner ear organs, and the target image comprises a HYDROPS image Multiplied with heavily T2-weighted MR cisternography (Hydrops-Mi2) image generated by synthesizing the MRC image and the Hydrops image.

6. An apparatus for measuring an endolymphatic hydrops ratio, the apparatus comprising a processor, wherein the processor obtains a plurality of frame images obtained by capturing inner ear organs, obtains a plurality of pieces of mask data corresponding to each of the plurality of frame images by inputting the plurality of frame images into a neural network, clusters the plurality of pieces of mask data according to the inner ear organs, obtains representative images according to the inner ear organs according to certain conditions, and overlaps a target image synthesized by using the plurality of frame images and the representative images according to the inner ear organs so as to measure an endolymphatic hydrops ratio.

7. The apparatus of claim 6, wherein the processor further generates three-dimensional (3D) segmentation corresponding to each of the inner ear organs by using the plurality of pieces of mask data clustered according to the inner ear organs and overlaps the target image and the 3D segmentation so as to measure an endolymphatic hydrops ratio.

8. The apparatus of claim 6, wherein the processor obtains mask data having a largest inner ear organ region included in each of the mask data among the plurality of pieces of mask data clustered according to the inner ear organs as representative images of the inner ear organs.

9. The apparatus of claim 6, wherein the processor overlaps the target image and the representative image according to the inner ear organs so as to obtain an endolymphatic hydrops detection image and measure an endolymphatic hydrops ration by using pixel data having negative values included in the endolymphatic hydrops detection image.

10. The apparatus of claim 6, wherein the plurality of frame images comprise frame images included in a MR cisternography (MRC) image obtained by capturing the inner ear organs, and the target image comprises a HYDROPS image Multiplied with heavily T2-weighted MR cisternography (Hydrops-Mi2) image generated by synthesizing the MRC image and the Hydrops image.

* * * * *